United States Patent [19]

McArthur

[11] Patent Number: 4,649,938
[45] Date of Patent: Mar. 17, 1987

[54] TISSUE-STIMULATING ELECTRODE HAVING SEALED, LOW-FRICTION EXTENDABLE/RETRACTABLE ACTIVE FIXATION MEANS

[76] Inventor: William A. McArthur, 27544 Lovage Ct., Saugus, Calif. 91350

[21] Appl. No.: 728,985

[22] Filed: Apr. 29, 1985

[51] Int. Cl.[4] .............................................. A61N 1/00
[52] U.S. Cl. .................................. 128/785; 128/419 P
[58] Field of Search .................. 128/303.13, 303.15, 128/419 P, 785, 790, 303.1, 786, 784, 642

[56] References Cited

U.S. PATENT DOCUMENTS

| | | | |
|---|---|---|---|
| 3,844,292 | 10/1974 | Boldue | 128/419 P |
| 4,026,301 | 3/1977 | Friedman et al. | 128/785 |
| 4,103,680 | 8/1978 | Yoon | 128/303.15 |
| 4,146,036 | 3/1979 | Dutcher et al. | 128/785 |
| 4,217,913 | 8/1980 | Dutcher | 128/419 P |
| 4,280,512 | 7/1981 | Karr et al. | 128/419 P |
| 4,381,013 | 8/1983 | Dutcher | 128/419 P |
| 4,463,765 | 8/1984 | Gold | 128/419 P |
| 4,475,560 | 10/1984 | Tarjan et al. | 128/785 |
| 4,570,642 | 2/1986 | Kane et al. | 128/785 |

FOREIGN PATENT DOCUMENTS

| | | | |
|---|---|---|---|
| 2539553 | 3/1977 | Fed. Rep. of Germany | 128/785 |
| 2806069 | 8/1979 | Fed. Rep. of Germany | 128/785 |
| 3230081 | 2/1984 | Fed. Rep. of Germany | 128/785 |

Primary Examiner—Edward M. Coven
Assistant Examiner—Max F. Hindenburg
Attorney, Agent, or Firm—Robert R. Meads; Bryant R. Gold

[57] ABSTRACT

An electrode tip (14) of a tissue-stimulating lead provides active fixation of the tip of body tissue. Tissue attachment means (34), within the electrode tip, are selectively extended so as to protrude from the tip upon application of an external force. Otherwise, biasing means (40), also within the electrode tip, urge the tissue attachment means to a retracted position within the tip. Extension and retraction of the tissue attachment means are realized through th use of a carrier bobbin (44), to one end of which the tissue attachment means are affixed. The carrier bobbin is movably inserted into a barrel (30) of the tip. An O-ring (38) placed around the circumfernce of the carrier bobbin, sized so as to make sealable contact with the inside barrel wall, seals th back end of the barrel and prevents fluids from flowing therein. This O-ring also rolls along the surface of the carrier bobbin and barrel wall as the bobbin moves within the barrel, thereby rducing friction associated with the movement of the bobbin. The carrier bobbin moves to its extended position upon application of an axial force. This axial force is selectively supplied by a stylet (20) that passes through a lume (56) of the lead.

18 Claims, 7 Drawing Figures

TISSUE-STIMULATING ELECTRODE HAVING SEALED, LOW-FRICTION EXTENDABLE/RETRACTABLE ACTIVE FIXATION MEANS

BACKGROUND OF THE INVENTION

The present invention relates to tissue-stimulating leads for use with a tissue-stimulating device, such as a cardiac pacemaker. More particularly, the present invention relates to a endocardial lead having a sealed, low-friction extendable/retractable screw-in electrode tip.

The advantages of screw-in cardiac leads are well known in the art. Such leads provide "active fixation" of the electrode tip to the tissue that is to be stimulated. This is in contrast to passive fixation devices, wherein the electrode tip may not be securely held against the body tissue until tissue ingrowth can occur. Epicardial leads employing screw-in tips have long been used in the art. In recent years, screw-in tips have also been used to secure endocardial leads. However, because the screw-in tip of such endocardial leads typically protrudes from a distal end of the lead, extreme care must be exercised when inserting the lead through a vein in order to prevent serious damage to vascular structure. Typically, such leads must be turned or rotated in a prescribed direction at the same time that they are being inserted into a vein in order to prevent the tip from engaging vascular structure at an undesired location.

Because of the problems and inherent dangers associated with a protruding screw-in tip of an endocardial lead during lead implantation, there have been developed in recent years endocardial leads having extendable/retractable screw-in electrode tips. A simple construction of such a lead incorporates a sliding carrier that is inserted into a tip housing at the distal end of the lead. A screw-in tip is attached to the distal end of the carrier. Prior to placement of the lead, the carrier is axially pushed, from the distal end of the lead, to a retracted position such that the screw-in tip does not protrude from the distal end. Once the lead has been positioned for placement, the screw-in tip is extended by axially pushing the carrier, from the proximal end of the lead through the use of a stylet, to an extended position so that the screw-in tip does protrude from the distal end.

Another type of extendable/retractable lead is the Medtronic Model 6957 lead. This lead incorporates a terminal pin/conductor-coil/electrode that rotates within polyether urethane insulation tubing. The screw-in tip is retracted within a housing at the distal end of the lead and remains in its retracted position until the distal tip is positioned at its desired tissue-stimulating location. Once at this location, the tip is extended by rotating the terminal pin approximately 8 to 10 turns, which rotation translates to approximately one turn at the distal or screw-in tip end of the lead, thereby effectuating the desired active fixation by screwing in the protruding screw-in tip.

It is also known in the art to use a lead similar to the Model 6957 described above, except that once positioned in its desired tissue-stimulating location, which positioning is typically realized through the aid of a conventional stylet, the conventional stylet is removed and a special stylet is inserted. This special stylet has a screw-driver like blade that engages a screw mechanism housed in the tubular housing at the distal end of the lead. To effectuate the desired extension of the screw-in tip of the lead, the lead is held steady while the special stylet is turned, thereby screwing the electrode-tip into the tissue at the desired location. In this particular embodiment, the fixation screw is not part of the electrode, that is, it is not electrically connected to the electrode tip. Rather, the screw-in tip serves merely as a mechanism for holding the distal tip, which includes a ring electrode, against the tissue.

Despite the advantages of the screw-in lead, numrous problems remain with its use. A relative large amount of external force is required in order to move the screw-in tip to its extended position. This is especially true for the simpler type constructions that utilize a sliding carrier to which the active fixation means is attached. These large forces are needed, of course, in order to overcome the friction that exists between the sliding carrier and the distal tip housing. Moreover, once the tissue has been penetrated by the screw-in tip, it is not uncommon for blood to leak from the fixation area into the lumen of the lead. The leaking of such blood into the lumen of the tissue-stimulating lead is undesirable. Further, especially when the tissue-stimulating lead is a cardiac lead that is positioned in heart tissue, the motion of the heart tissue (as the heart beats) can cause some loosening of the lead. Such loosening is not major, especially relative to passive fixation leads, but any amount of loosening can eventually allow scar tissue to build up between the electrode tip and the tissue. This scar tissue disadvantageously represents an increase in the resistance of the tissue-stimulating system, thereby necessitating an increase in the power level of the stimulating pulse in order to effectuate the desired stimulation. While modern tissue-stimulating devices can readily accomodate an increase in the stimulating pulse power level, such increases are disfavored because they represent an added drain on the batteries of such devices, thereby decreasing their useful life.

In view of the above, it is evident that there is a need in the art for an active fixation tissue-stimulating lead that avoids the problems of applying large forces in order to move the screw-in tip to its extended position, leaking of blood into the lumen of the lead during installation, and the loosening of the lead subsequent to installation. The present invention addresses these and other problems.

SUMMARY OF THE INVENTION

It is an object of the present invention to provide an improved tissue-stimulating lead having extendable/retractable active fixation means. More particularly, it is an object of the present invention to provide an endocardial lead having a low friction extendable/retractable active fixation means.

It is a further object of the present invention to provide such an improved tissue-stimulating lead that further prevents the leading of blood into the lumen of the lead.

Still a further object of the invention is to provide such a lead that also includes biasing means for urging the electrode tip back to its retracted position, which biasing means thereby serves to hold the lead securely against the body tissue once it has been attached thereto.

Yet another object of the present invention is to provide an improved endocardial screw-in lead incorporating all of the objects described above while still being very simple and inexpensive to manufacture, yet that offers very reliable operation during implantation, normal use, and any subsequent removals and reimplantations that may be required.

A further object of the present invention is to provide a method of implanting such an improved tissue-stimulating lead in cardiac tissue.

Another object of the invention is to provide such a method of implantation that allows the lead to be optimally positioned within the heart prior to the active fixation thereof.

The above and other objects of the present invention are realized through the use of a tissue-stimulating lead having a ring electrode at the distal end thereof. Tissue attachment means, such as a helix screw-in tip, are housed within a barrel inside of the ring electrode, and are selectively extended so as to protrude from the ring electrode upon application of an external force. Biasing means, also housed within the electrode tip, urge the tissue attachment means to a retracted position within the barrel in the absence of an externally applied force. Extension and retraction through the use of a carrier bobbin that is slidably inserted into the barrel of the electrode tip. The tissue attachment means are connected to the distal end of the carrier bobbin. An O-ring placed around the circumference of the carrier bobbin, and sized so as to make sealable contact with the inside barrel wall, seals the back end of the barrel and prevents fluids, such as blood, from flowing therein. Advantageously, this O-ring also rolls along the surface of the carrier bobbin and barrel wall as the bobbin axially moves within the barrel, thereby significantly reducing the friction associated with the sliding of the bobbin. The carrier bobbin slides to its extended position upon application of an axial force that is selectively applied through the use of a conventional stylet that passes through a lumen of the lead. This stylet is inserted into the lead until its distal tip engages a proximal end of the carrier bobbin. Then, an axial force applied at the proximal end of the stylet (tending to push the stylet further into the lumen) translates to an axial force at the carrier bobbin which, if sufficient to overcome the biasing means that tends to hold the carrier bobbin in its retracted position, slides the carrier bobbin to its extended position. Once in its extended position, the active fixation means protrude from the ring electrode fixation means protrude from the ring electrode and are available to actively fix the entire distal tip of the electrode to body tissue.

The method of attaching a lead having the low-friction extendable/retractable active fixation means of the present invention includes inserting the lead into the general body tissue area to which it is be attached, such insertion being carried out with the active fixation means in its retracted position; moving the lead about within this general area of fixation until an optimal fixation location is determined; sliding the carrier bobbin to its extended position by applying an axial force to a stylet inserted into the lead; and rotating the lead at its distal end, which rotation transfers a sufficient torque to the distal end of the lead so that the active fixation means can be screwed-in to the tissue at the desired location.

As indicated, the O-ring that is placed about the circumference of the carrier bobbin not only signficantly reduces the amount of friction that is associated with axial movement of the bobbin, but also provides a very effective sealing mechanism to prevent blood from leaking into a back end of the barrel. Advantageously, the amount of force required to move the bobbin to its extended position is only about ¼ or 1/5 of that required to move other extendable tips to their extended position. Further, the biasing means that is employed to urge the carrier bobbin to its retracted position, not only serves to hold the bobbin in its retracted position while the lead is being intravenously inserted or otherwise placed into the desired stimulation area, but also serves to secure the electrode tip against the tissue once attachment of the active fixation means has been completed.

BRIEF DESCRIPTION OF DRAWINGS

The above and other objects, features, and advantages of the present invention will be more apparent from the following more particular description thereof presented in conjunction with the following drawings, wherein.

DETAILED DESCRIPTION OF THE INVENTION

The following description is of the best presently contemplated mode of carrying out the invention. This description is not to be taken in a limiting sense but is made merely for the purpose of describing the general principles of the invention. The scope of the invention should be determined with reference to the attached claims.

The invention will be described with reference to the figures, wherein like numerals are used to describe like parts throughout.

Figures 1, 7:
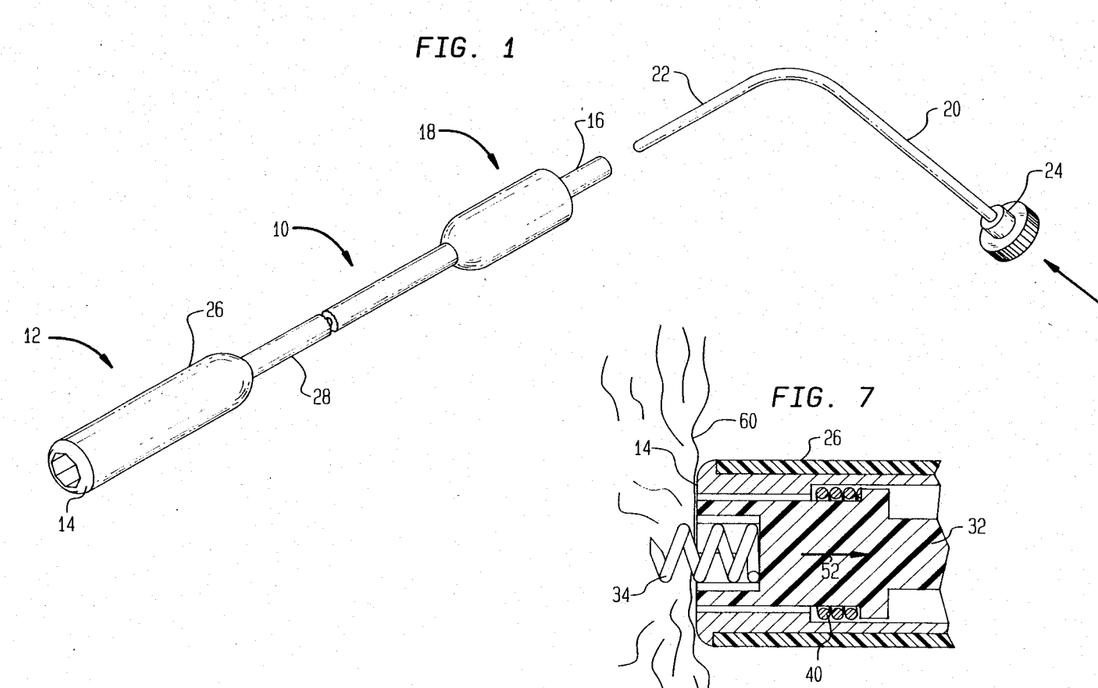
FIG. 1 is a tissue-stimulating lead in accordance with the present invention, and illustrates how a stylet is inserted thereinto.
FIG. 7 is a side sectional view showing the tip of the electrode attached to tissue, and illustrates how the biasing means of the electrode tip helds maintain tight contact between the electrode and the tissue to which the electrode tip has been attached.

Referring first to FIG. 1, there is shown an endocardial lead 10. At a distal end 12 of the lead 10 a ring electrode 14 is positioned so that at least one surface thereof is exposed. This exposed surface is intended for contact with body tissue, and it is through this exposed surface that the stimulating pulses electrically make contact with the tissue. The ring electrode 14 is electrically connected to a connecting pin 16 at a proximal end 18 of the lead 10. This electrical connection is realized through the use of a helically wound conductor, which type of conductor advantageously allows the lead to remain very flexible yet sufficiently stiff to allow its insertio intravensously into the heart. Typically, the helically wound conductor is coated with a suitable electrical insulating material 28, such as silicon rubber, that is compatible with body fluids and the general invivo environment in which the lead is used. Unless specified otherwise, and with the exception of the distal end 12, which distan end is described more fully below, the construction of the body of the lead 10, and the proximal end 18 of the lead 10, are conventional.

Also shown in FIG. 1 is a stylet 20, which stylet also has a distal end 22 and a proximal end 24. The stylet is sized for insertion into a lumen of the lead 10. The stylet 20 is likewise flexible, and this is emphasized in FIG. 1 by showing a bend therein.

Figure 2:
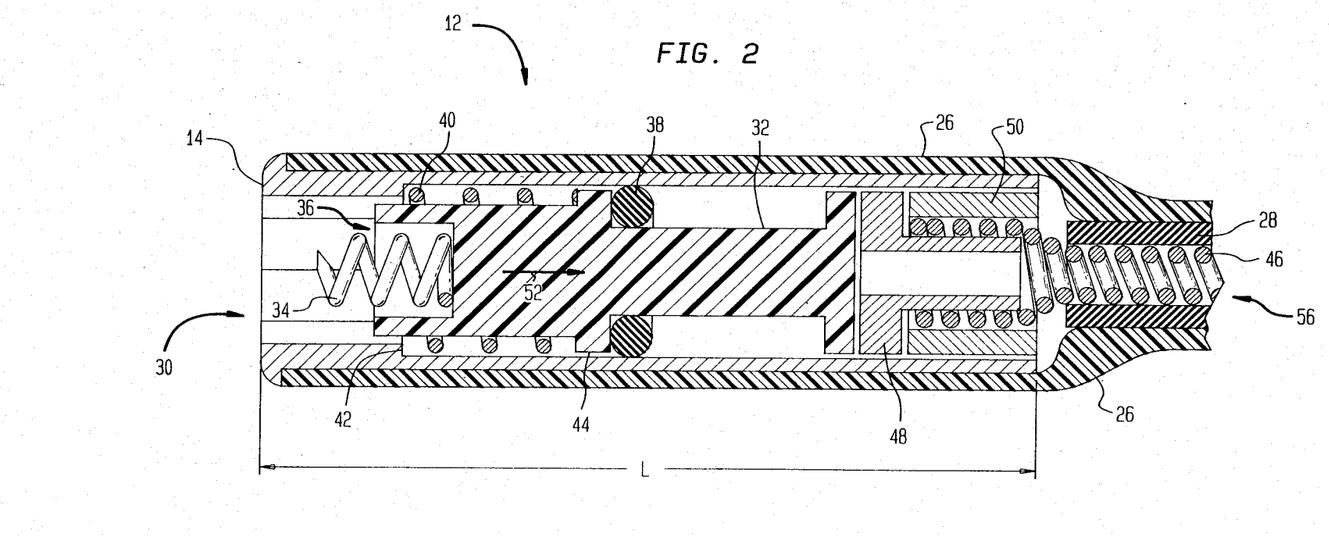
FIG. 2 shows an enlarged cross-sectional view of the distal end of the lead of FIG. 1, showing the screw-in fixation helix in its retracted position.

Referring next to FIG. 2, there is shown a sectional view of the distal end 12 of the lead 10. As seen in FIG. 2, the ring electrode 14 comprises a conductive ring or band having a length L. Only the extreme distal end of the ring electrode 14 is exposed, the remainder thereof being insulated with a layer or thickness of silicon rubber 26, or other suitable electrically insulating material. This insulating silicone rubber 26 covers the entire length of the distal end 12, as explained, with the exception of the extreme distal end of the ring electrode 14. This insulating layer 26 overlaps with a similar insulating silicone rubber layer 28 that encompasses the body of the lead 10, as shown on the right of FIG. 2.

As indicated in FIG. 2, the ring electrode 14 is hollowed out so as to define a barrel 30. A carrier bobbin 32 is slidably inserted into the barrel 30. A helix screw-in tip 34 is secured to a cavity or hole 36 at a distal end of the bobbin 32. An O-ring is placed around the circumference of the bobbin 32 and makes sealable contact between the bobbin 32 and the walls of the barrel 30. A helical spring 40 is likewise placed around the circumference of the bobbin 32 and is inserted under compression between a ridge 42 in the barrel wall and a flange 44 of the bobbin 32.

Figure 3:
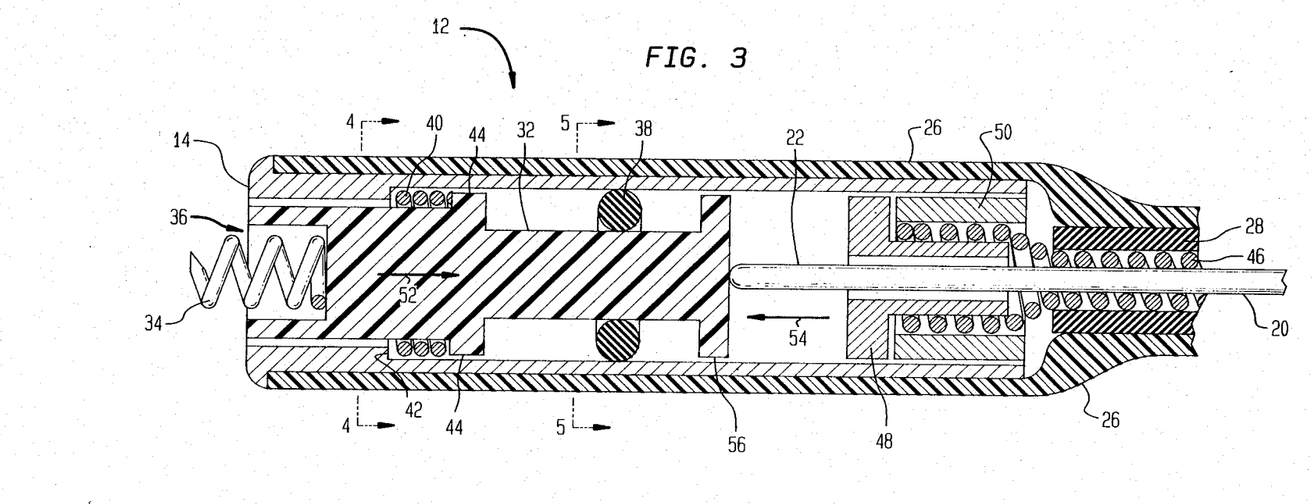
FIG. 3 is a cross sectional view as in FIG. 2 except that the screw-in fixation helix has been moved to its extended position by a stylet that has been inserted into a lumen of the lead.

The helically wound conductor, designated as 46 in FIGS. 2 and 3, is secured to a crimp insert 48 by a crimp ring or sleeve 50. This assembly of the crimp insert 48 and the crimp ring 50 is electrically connected to the proximal end of the barrel 14.

The carrier bobbin 32 is shown in FIG. 2 in its retracted position. In this position, the helix screw-in tip 34 is completely retracted within the barrel 30 of the ring electrode 14. This retracted position is maintained by the biasing forces supplied by the spring 40, which spring, being under compression, exerts an axial force against the flange 44 of the carrier bobbin 32 in the direction shown by the arrow 52.

Referring next to FIG. 3, there is shown a sectional view of the distal end 12 of the lead 10 with the carrier bobbin 32 slid to its extended position. In this position, the helix screw-in tip 34 protrudes out from the ring electrode 14. The axial force provided by the compressed spring 40, represented by the arrow 52 (which force 52, as explained above, tends to maintain the carrier bobbin 32 in its retracted position), is overcome by an opposing axial force, represented by the arrow 54. This force 54 is applied by the distal end 22 of the stylet 20, inserted into a lumen 56 of the lead 10.

Advantageously, axial movement of the carrier bobbin 32 is facilitated by the presence of the sealing O-ring 38. As the distal tip 22 of the stylet 20 engages a proximal end of the carrier bobbin 32, the O-ring 38 rolls along the surface of the bobbin 30 and the inner barrel wall of the electrode 14. As best indicated in FIG. 3, an end flang 56 at the proximal end of the bobbin 32 prevents the O-ring 38 from rolling off the end thereof. The rolling of the O-ring 38 significantly reduces the amount of axial force 54 that is needed in order to slide the bobbin 32 into its extended position. Further, as indicated previously, the O-ring also seals the back or proximal end of the barrel 30 to prevent fluids from flowing thereinto.

Figure 4:
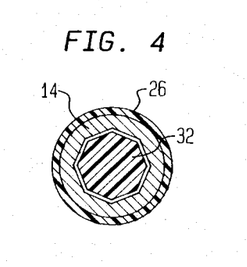
FIG. 4 is a sectional view taken along the line 4—4 of FIG. 3.
Figure 5:
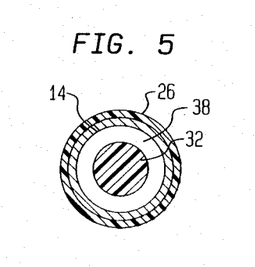
FIG. 5 is a sectional view taken along the line 5—5 of FIG. 3.

The carrier bobbin 32 is prevented from rotating within the barrel 30 through use of an octagonal cross-sectional shape of the bobbin 32 and the barrel 30 at their respective distal ends, as best shown in the sectional view of FIG. 4. However, this octagonal cross-sectional shape is discontinued rearwardly (towards the right in the figures) from the flange 44 of the bobbin 32, and rearwardly from the flange 42 of the barrel 30, as illustrated in the sectional view of FIG. 5. This construction allows the round O-ring 38 to freely roll, while still providing the desired sealing function, as the carrier bobbin 32 is slid from one position to another. The octagonal cross-sectional shape advantageously prevents the carrier from rotating within the barrel as the screw-in tip 34 is affixed to body tissue. It is contemplated that other keyed-type constructions could be used to achieve this same result.

Figure 6:
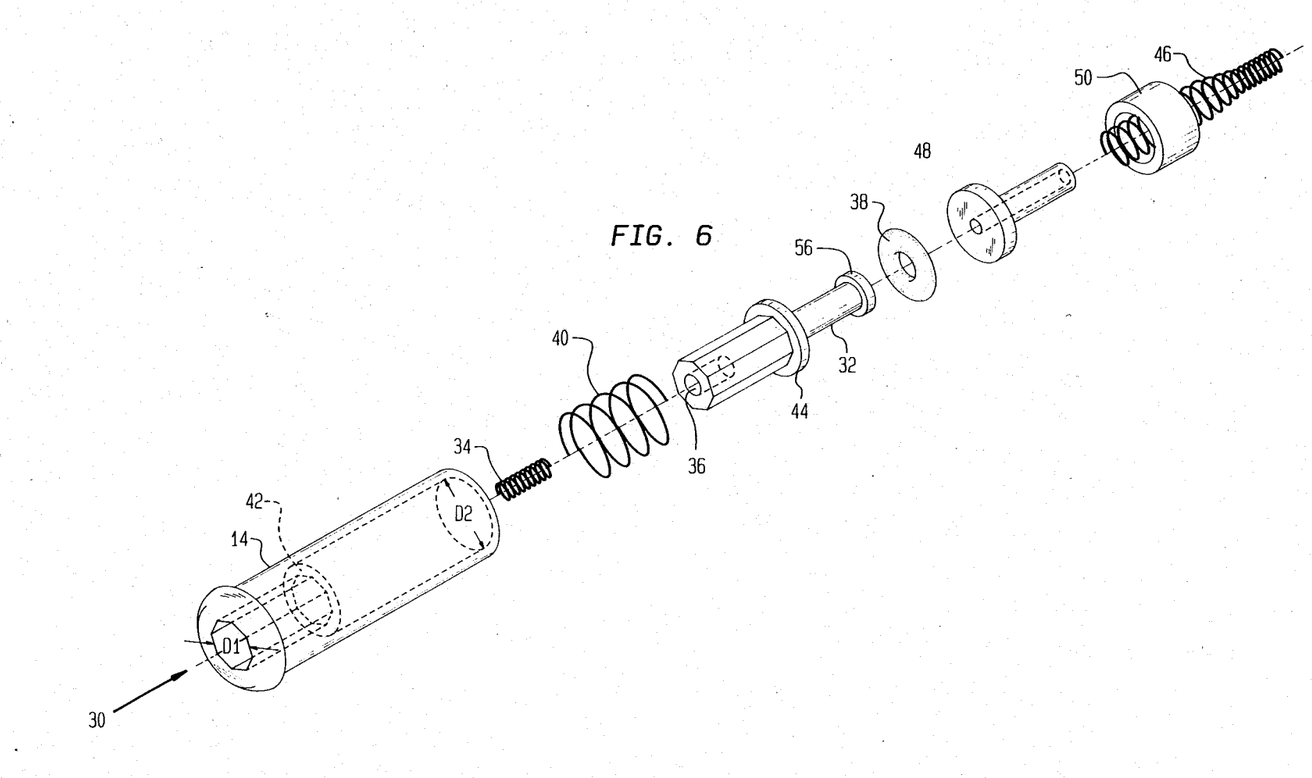
FIG. 6 is an exploded assembly drawing of the electrode tip of FIGS. 2 and 3.

Next, referring to FIG. 6, an exploded assembly drawing of the sealable, low-friction extendable/retractable electrode tip of the present invention is illustrated. Now included in FIG. 6 are the electrically insulating layers 26 and 28 that are placed around the distal tip 12 and body of the lead 10, respectively. Referring to FIG. 6, the manner of assembly of the electrode tip of the present invention is best illustrated. The ring electrode 14, in the preferred embodiment, is fabricated from a rod of platinum iridium. This rod has an outer diameter of 0.130 inches, although any appropriate size rod could be used. This rod is bored or otherwise hollowed out with a hole having a diameter of approximately D1. A second operation then counter bores a hole having a diameter D2 (greater than D1) from the proximal end of the ring electrode 14. Suitable techniques, known to those in the art, are then used to convert the first hole, having diameter D1, into the octagonal cross-sectional shape shown in FIG. 4.

The carrier bobbin 32 is made from a non-conducting material, such as polysulfone. The distal end of the carrier 32 is formed to have an octagonal cross-sectional that matches the octagonal cross-sectional shape of the distal end of the barrel 30. The remaining length of the carrier bobbin 32, between the flange 44 and the end flange 56, is made to have a smooth rounded surface. The O-ring 38, made from a suitable resilient material, such as silicone rubber, is stretched over the end flange 56 so that is can roll along the length of the body of the carrier bobbin 32 betwen the flanges 44 and 56. The helix screw-in tip 34 is secured inside the bored hole 36 at the distal end of the bobbin 32 through conventional means. The biasing spring 40 is slid over the distal end of the bobbin 32. This carrier bobbin assembly is then slid into the back end of the barrel 30. The conductor 46 is slid over a shaft portion of the crimped insert 48, and the crimped ring or sleeve 50 is then slid over both the conductor 46 and the shaft of the crimped insert 48. This assembly is likewise slid into the back end of the barrel 30 of the ring electrode 14. A crimping operation applied to the proximal end of the barrel 14 then serves to electrically connect the conductor 46 to the crimped insert 48, the crimped ring or sleeve 50, and the ring electrode 14. Other suitable bonding techniques, assuring good electrical contact, could likewise be used, such as spot welding. After the assembly of the electrode tip has been completed as thus described, conventional means are used to apply the insulating silicon rubber sheath 26 around the distal end, as well as the insulating layer 28 applied to the body of the lead.

Referring next to FIG. 7, a partial view of the electrode tip of the present invention is shown as attached to body tissue 60. Advantageously, the same spring force, represented by the arrow 52, that urges the carrier bobbin 32 into its retracted position, also serves to urge the ring electrode 14 securely against the body tissue 60 once the helix screw-in tip 34 has been screwed into the body tissue 60. This action thus helps prevent the helix screw-in tip 34 from coming loose subsequent to attachment. However, should there be a need to remove the electrode tip from the tissue 60 subsequent to implantation thereof, the lead can be unscrewed by twisting the lead without causing serious damage to the tissue 60.

In order to facilitate the attachment of the helix screw-in tip 34 to the body tissue 60, it is contemplated that the spring constant associated with the helically wound conductor 46 be selected to efficiently transfer torque from the proximal end 18 of the lead 10 to the distal end 12. In the preferred embodiment, about 5 turns of the proximal end of the lead are needed to achieve a full 2 turn penetration of the screw-in tip 34. This compares with about 10–12 turns that are needed to effectuate fixation in other available lead designs.

The method of installing a screw-in lead of the type described above includes the steps of:

(1) Inserting the lead, with its screw-in electrode tip in its retracted position, intraveneously into the desired tissue stimulating area of the body.

(2) Moving the lead around to various positions within the desired tissue-stimulating area in order to map the response of the tissue to applied stimulation pulses. This action allows an optimum location of lead placement to be selected. This step includes holding the ring electrode at a desired location, through the use of a stylet for example, and providing a stimulating pulse of sufficient signal power to produce the desired stimulus. Techniques are known in the art for determining a proper power stimulation level. Once the tissue-stimulating area has been mapped in this fashion, the area requiring the lowest stimulating pulse threshold can be selected, thereby achieving the desired stimulating results without causing unnecessary drain on the battery on the stimulating device.

(3) Applying an axial force, through the use of a conventional stylet, of sufficient magnitude to overcome the biasing force that holds the screw-in helix tip in its retracted position, thereby sliding the carrier bobbin to its extended position.

(4) While maintaining the axial force supplied in step (3), twisting the lead by grabbing the proximal end thereof and rotating it approximately 5 turns, thereby allowing the now-protruding screw-in helix tip to be screwed-in to the body tissue.

(5) Removing the stylet from the lumen of the lead, thereby allowing the biasing force within the electrode tip to help hold the ring electrode securely against the tissue that is to be stimulated.

Should it be necessary to reposition the lead once attached, repositioning can be readily accomplished be merely unscrewing the helix tip by rotating the proximal end of the lead 10 in the opposite direction from that used to screw in the tip. Once the lead is no longer affixed to body tissue, the protruding helix tip will be urged into its retracted position by the internal biasing means. Advantageously, once the lead has been unscrewed from the body tissue in this fashion, it may be repositioned to a new location and resecured, or removed.

The force 52 exerted by the spring 40 at its point of maximum compression should be a light force sufficient to retract the carrier bobbin or hold the ring electrode in tight contact with body tissue without tending to pull the body tissue inside of the barrel 30. For the preferred embodiment described herein, the spring 40 exerts a force of approximately 15 grams at its point of maximum compression.

While fixation of the helix tip to body tissue in accordance with the embodiment described herein contemplates rotating the lead, which lead rotation causes the helix tip to rotate through the use of some sort of keying device (such as the matching octagonal cross-sectional shapes of the distal ends of the carrier bobbin 32 and barrel 30), the invention also contemplates that other means could be used to achieve the desired helix tip rotation. For example, the carrier bobbin could be allowed to rotate within the barrel 30 of the ring electrode and the tip of a special stylet could be keyed with the carrier bobbin 32 so that rotation of the stylet would cause rotation of the bobbin. In accordance with this alternative embodiment, once the electrode tip was postitioned at its desired tissue-stimulating location, the special stylet could be lockably engaged with the carrier bobbin 32, and the stylet would be rotated, rather than the lead, in order to achieve the desired rotation of the screw-in tip.

It is noted that for the preferred embodiment illustrated in connection with FIGS. 2–7 that the screw-in helix tip 34 is electrically insulated from the ring electrode 14. However, the invention is not intended to be limited to an electrically-isolated screw-in tip. The principles of the invention providing an invivo, sealed, low-friction extendable/retractable active fixation means, could be equally applied to a lead wherein the screw-in tip were electrically connected to the lead conductor.

While the invention herein disclosed has been described by means of specific embodiments and applications thereof, numerous modifications and variations could be made thereto by those skilled in the art without departing from the spirit and scope of the present invention. It is therefore to be understood that within the scope of the appended claims, the invention may be practiced otherwise then as specifically described herein.

What is claimed is:

1. An electrode tip for use with a tissue-stimulating lead comprising:
   an electrode connected to a distal end of said lead;
   carrier means axially inserted into a barrel of said electrode;
   tissue attachment means affixed to a distal end of said carrier means for securely holding the distal end of said carrier means to desired tissue, said tissue attachment means protruding from said barrel when said carrier means assumes an extended position, and said tissue attachment means remaining inside of said barrel when said carrier means assumes a retracted position;
   movement means for selectively moving the carrier means between its retracted position and its extended position; and sealing/friction-reducing means fitted around the circumference of said carrier means for preventing fluid flow around said carrier means into a proximal end of said barrel, and for reducing friction between said carrier means and said barrel as said carrier moves between its retracted and extended positions, said sealing/friction-reducing means being axially movable with respect to both the barrel of said electrode and said carrier means.

2. The electrode tip of claim 1 wherein said sealing/friction-reducing means rolls along the surface of said carrier means and an inner wall of said barrel as said carrier means moves between its retracted and extended positions.

3. The electrode tip of claim 2 wherein said sealing means comprises an O-ring placed around the outer circumference of said carrier means, said O-ring being sized so as to make sealable contact with said carrier means and an inside circumferential wall of said barrel.

4. The electrode tip of claim 2 further including biasing means housed therewithin for resiliently maintaining the carrier means in its retracted position, which biasing means further helps hold the ring electrode against the desired tissue once the tissue attachment means has been secured thereto.

5. The electrode tip of claim 4 wherein said biasing means exerts a force urging said carrier means to its retracted position with a maximum force that is less than a force that would pull body tissue into the barrel of the electrode.

6. The electrode tip of claim 4 wherein said movement means comprises means for selectively applying an axial force to said carrier means opposing said biasing means.

7. The elctrode tip of claim 6 wherein said lead includes a helically-wound conductor having a lumen through the length thereof and wherein said means for selectively applying an axial force to said carrier means comprises:
means for inserting a stylet through said lumen until a distal tip of said stylet engages a proximal end of said carrier means; and
means for applying an axial force to said stylet the continued application of said axial force, if of a magnitude greater than the opposing force asserted by said biasing means, causes the carrier means to slide to its extended position.

8. The electrode tip of claim 7 wherein said tissue attachment means comprises a screw-in fixation helix, which fixation helix is affixed to the desired tissue by rotating the lead at the same time that the axial force is applied to said stylet.

9. A tissue-stimulating lead comprising:
a flexible conductor having a proximal end adapted for connection to a tissue-stimulating device and a distal end adapted for contact with desired tissue;
a stimulating tip connected to the distal end of the conductor, said stimulating tip having a barrel therein;
a movable carrier bobbin inserted into said barrel;
tissue attachment means affixed to one end of said carrier bobbin, said tissue attachment means protruding from said barrel whenever said carrier bobbin assumes an extended position, and said tissue attachment means remaining inside of said barrel whenever said carrier bobbin assumes a retracted position;
extension means for selectively applying forces to the carrier bobbin that position said carrier bobbin in its extended position, thereby facilitating the attachment of said tissue attachment means to the desired tissue; and
retraction means within said stimulating tip for continuously urging the carrier bobbin back towards its retracted position; said retraction means helping to maintain contact between said tip electrode and the desired tissue once the desired tissue has been attached to the tissue attachment means.

10. The tissue-stimulating lead of claim 9 further including friction reducing means for reducing the friction between said carrier bobbin and the barrel, thereby facilitating the movement of the carrier bobbin as it moves between its extended and retracted positions within said barrel.

11. The tissue-stimulating lead of claim 10 wherein said friction reducing means are further for preventing fluid flow around said carrier bobbin into a back portion of said barrel.

12. The tissue-stimulating lead of claim 11 wherein said friction reducing means comprises an O-ring that is placed around the periphery of said carrier bobbin.

13. The tissue-stimulating lead of claim 12 wherein said O-ring rolls between the surfaces of said carrier bobbin and said barrel as said carrier bobbin moves in and out of said barrel.

14. The tissue-stimulating lead of claim 9 wherein said extension means comprises means for applying a force that urges said carrier bobbin into its extended position.

15. The tissue-stimulating lead of claim 14 wherein the flexible conductor of said lead has a lumen therein; and wherein said means for applying a force comprises means for removably inserting a stylet into the lumen of said conductor until a distal end of said stylet engages said carrier bobbin, and means for applying an axial force to a proximal end of said stylet.

16. The tissue-stimulating lead of claim 15 wherein said retraction means comprises a spring engaged with said carrier bobbin and barrel, said spring being biased so as to urge the carrier bobbin to its retracted position with a force that does not exceed a prescribed value, said prescribed value being less than a force that would cause body tissue to be pulled inside of said barrel by said retraction means.

17. A method for attaching a tissue-stimulating lead to body tissue, said tissue-stimulating lead comprising a flexible conductor having a lumen therein, and having a tip electrode attached to a distal end thereof, and further having tissue attachment means connected to said tip, internal biasing means housed within the distal end of said lead for maintaining the tissue attachment means in a non-protruding recessed position within said tip, and means for extending said tissue attachment means to a protruding position from said tip upon application of an external force, said method comprising the steps of:
(a) positioning the tip electrode of said lead adjacent the tissue to which it is to be attached;
(b) applying an external force to the means for extending the tissue attachment means to cause said tissue attachment means to protrude from said tip;
(c) affixing said protruding tissue attachment means to the body tissue; and
(d) removing the external force applied in step (b), whereupon said internal biasing means helps maintain the tip electrode in contact with the attached body tissue.

18. The method of claim 17 wherein step (b) of applying an external force to the means for extending the tissue attachment means includes removably inserting a stylet into the lumen of said lead, and applying an axial force to a proximal end of said stylet, said axial force being transferred through said stylet to a distal end thereof, whereat said force is used to effectuate the protrusion of said tissue attachment means.

* * * * *